United States Patent [19]

Sato et al.

[11] Patent Number: 4,966,978

[45] Date of Patent: Oct. 30, 1990

[54] PROCESS FOR SEPARATING INDOLE IN REFINED FORM

[75] Inventors: Yoshiki Sato; Yoshitaka Yamamoto, both of Tsukuba; Yutaka Mito, Ibaraki; Harumasa Tanabe, Kobe, all of Japan

[73] Assignee: Kabushiki Kaisha Kobe Seiko Sho, Kobe, Japan

[21] Appl. No.: 363,084

[22] Filed: Jun. 8, 1989

[30] Foreign Application Priority Data

Jun. 8, 1988 [JP] Japan ................................ 63-140730

[51] Int. Cl.[5] ............................................ C07D 209/08

[52] U.S. Cl. ..................................................... 548/469

[58] Field of Search .......................................... 548/469

[56] References Cited

U.S. PATENT DOCUMENTS 2,982,771 5/1961 Bond, Jr. ............................ 548/469

4,769,474 9/1988 Miyahara et al. .............. 548/469 X

FOREIGN PATENT DOCUMENTS 0062565 4/1984 Japan .................................. 548/469

0164775 9/1984 Japan .................................. 548/469

1063654 4/1986 Japan .................................. 548/469

1140563 6/1986 Japan .................................. 548/469

1151170 7/1986 Japan .................................. 548/469

*Primary Examiner*—Joseph Paul Brust

*Attorney, Agent, or Firm*—Oblon, Spivak, McClelland, Maier & Neustadt

[57] ABSTRACT

Described herein is a process for separating solid indole in refined form with an extremely high degree of purity from a mixture containing more than 50 wt % of indole, in which a pressure of 700–2500 atms is applied to the mixture in a high pressure vessel, and solid-liquid separation is effected continuedly under pressurized state with an initial temperature in the range of 50°–65° C.

3 Claims, 1 Drawing Sheet

PROCESS FOR SEPARATING INDOLE IN REFINED FORM

BACKGROUND OF THE INVENTION

1. Field of the Invention

This invention relates to a process for separating indole in refined form, and more particularly to a process for separating indole in refined form from an indole-containing mixture by pressurized crystallization. Solid-liquid separation is carried out under pressure, yielding indole of high purity in solid form.

2. Prior Art

Indole is extremely important as a raw material for fragrances and flavors. Indoles is normally required to have high purity to function as a fragrance to a sufficient degree.

Heretofore, for the production of indole of high purity, it has been the usual practice to resort to a method (conventional method A) using coal tar or the like as a crude material, condensing the crude material, and then repeating the separation and refinement by a cooling crystallization process, ion-exchange process or adsorption process a method (conventional method B) forms indole into an alkali metal salt by an alkali fusion process or the like. After separating the metal salt, the separation is repeated with refinement by a cooling crystallization process or the like.

For instance, Japanese Laid-Open patent application No. 56-65868 proposes a method of separating indole from a fraction with a boiling point of 220°-270° C., which is obtained by distillation of coal. The indole is adsorbed and then desorbed by the use of anisole or the like.

Japanese Laid-Open patent application No. 57-98259 proposes a method of distilling crude indole, obtained from a coal tar fraction, until concentration of coexisting methylindole reaches a specific range, and producing refined indole by continuous cooling crystallization.

Described in Japanese Laid patent application No. 61-234789 is a method of adsorbing indole by passing an indole-containing tryptophane reaction liquid through a cation-exchange resin, and eluting indole with a hydrous organic solvent to obtain indole of high purity.

Further, an indole separating and refining method is described in "Newest Organic Chemistry 2", page 336, by Fezer, in which indole is formed into sodium salt by an alkali fusion process and then separated in refined form from the salt by a cooling crystallization process.

However, the above-mentioned conventional indole separating and refining methods have various problems as discussed below.

Namely, in the cooling crystallization process employed in the conventional method A, indole is crystallized out by cooling an indole-containing mixture, followed by solid-liquid separation. Therefore, it is necessary in the cooling crystallization stage to grow crystals which are suitable for the solid-liquid separation. That is to say, the cooling crystallization condition has to be strictly controlled. This gives rise to a problem that the operation for the cooling crystallization takes a long time. Besides, there is also a problem that scales are likely to deposit and its prevention makes the operation of cooling crystallization difficult. In addition, it is generally difficult to separate the crystal from the mother liquor, and this makes it difficult to obtain indole of high purity.

In the ion exchange process, a difficulty is encountered in separating indole form an eluent which is used for eluting indole adsorbed on an ion-exchange resin, and therefore the separation involves a complicated process. There is also a problem that regeneration or replacement of the ion-exchange resin further complicates the process.

The adsorption process has a problem in that the separation of indole from a zeolite desorbing agent is often difficult. Another problem is that regeneration or replacement of the adsorbent also complicates the process.

In the conventional method B, highly dangerous metallic sodium is used turn indole into an alkali metal salt by the alkali fusion process, wherein raising the temperature to induce the reaction involves safety problems. Despite the dangerous operation, the indole which is obtained after separation and refinement is low in purity, and needs a further refining operation.

Because of the above-discussed problems, the conventional indole separating and refining processes have not yet succeeded in realizing industrial production of high purity indole.

SUMMARY OF THE INVENTION

One object of this invention is to eliminate the above-mentioned problems of the prior art processes, more particularly, to provide a process for separating, in refined form indole of high purity in a simplified manner. A further object is to permit a separation and refinement easily, in a shortened period of time by an operation which is also improved in safety.

In accordance with the present invention, the above-mentioned objectives are achieved by an indole separating and refining process which, in one aspect of the invention, includes feeding a mixture containing more than 50 wt % of indole to a high pressure vessel, crystallizing out indole by applying pressure to the mixture in the vessel, conducting solid-liquid separation continuedly in pressurized state, and taking out indole of high purity in solid state, characterized in that a pressure of 700-2500 atms. is applied for the crystallization, and the initial temperature of the solid-liquid separation is 50°-65° C. According to another aspect of the invention, the process of separating indole in refined form includes a step of precooling the starting mixture into a slurry form containing less than 30 wt % of crystalline indole, prior to feeding the mixture to the high pressure vessel. According to still another aspect of the invention the process of separating in refined form includes a step of conducting the solid-liquid separation with continuous or stepwise pressure reductions.

As described hereinbefore, the process of separating indole in refined form is a pressurized crystallization process crystallizing out a particular component in refined form, which mainly resorts to the action of pressure for obtaining crystals of a particular composition and for the solid-liquid separation. This pressurized crystallization process is a separation and refinement technology which has great possibilities of application to materials which are difficult to separate by conventional distillation or cooling crystallization processes in general, and which facilitates to obtain products of high purity at a high yield while permitting reductions of energy consumption. However, to make the most of the benefits of this pressurized crystallization process in an actual application, it is necessary to select the pressurized crystallization conditions which correspond to a particular purpose of application. These conditions remain unknown in many aspects, and are completely unknown in case of application to the indole separation and refining process in the absence of records of successful applications in this regard.

The above and other objects, features and advantages of the invention will become apparent from the following description and the appended claims, taken conjunction with the accompanying drawing.

BRIEF DESCRIPTION OF THE DRAWING

The sole FIGURE shows major components of a small-size pressure crystallization equipments employed in Examples.

PARTICULAR DESCRIPTION OF THE INVENTION

Figure 1:
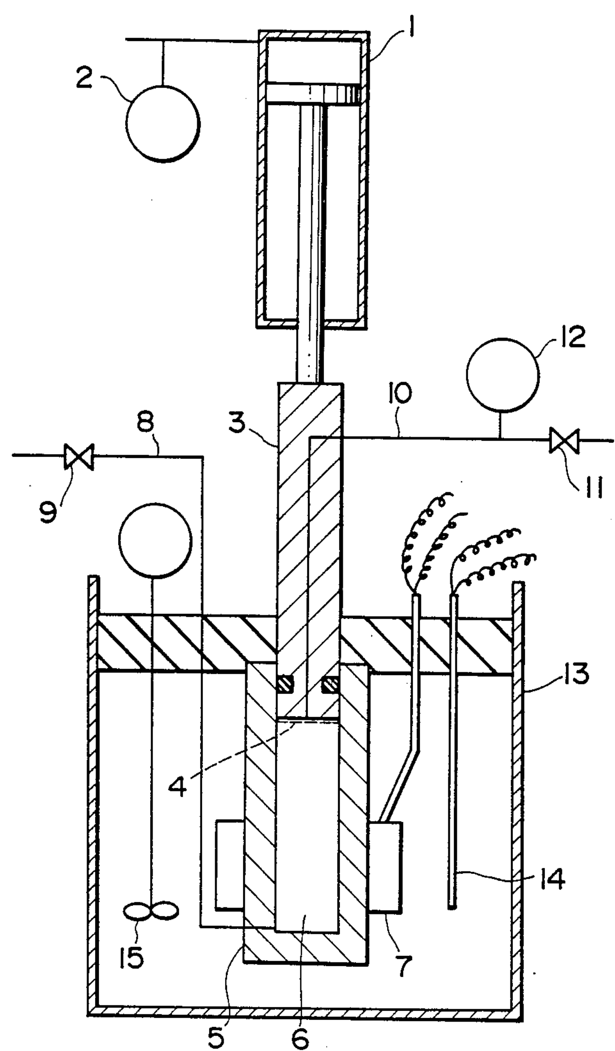

The present invention has been achieved on the basis of findings obtained as a result of extensive studies which were conducted on the pressurized crystallization conditions with a view to applying the pressurized crystallization process to separation and refinement of indole.

Namely, the process of separating indole in refined form according to the invention comprises, as described hereinbefore, feeding a mixture containing more than 50 wt % of indole to a high pressure vessel, pressurizing the mixture in the vessel to crystallize indole, conducting solid-liquid separation continuedly under pressurized condition, and taking out indole of high purity in solid state.

As the mixture of the feed material is pressurized to a certain level, crystallization of indole in the starting material progresses, immediately reaching a certain solid-liquid ratio (a saturated state). The solid (indole) which is produced at this time has an extremely high degree of purity. In the succeeding solid-liquid separation under pressure, the crystal grains are formed into a single large lumpy solid along the contour of the high pressure vessel. Nextly, the thus formed solid is taken out to obtain indole of high purity.

The mixture to be fed to the high pressure vessel should contain indole in an amount greater than 50 wt % that it can be taken out in solid state as described hereinbefore. When the mixture contains less than 50 wt %, the crystallization of indole progresses, but small growth of crystal deteriorates the solid-liquid separation, the crystal grains taking a sherbet-like form instead of forming a lumpy solid. This makes it difficult to obtain indole in solid state.

A pressure of 700–2500 atms. is applied for the above-described crystallization, because, under a pressure smaller than 700 atms, the crystallization of indole barely takes place, and, if took place, the crystal grains would be small in size and amount and difficult to take out in solid state. On the other hand, when the applied pressure exceeds 2500 atms., crystallization of components other than indole takes place, lowering the purity of solid indole of the ultimate product to a marked degree.

The initial temperature of the solid-liquid separation should be in the range of 50°–65° C., for the following reasons. Namely, when conducting sweat-washing, the extent of sweat-washing effect will be lowered abruptly if lower than 50° C., making it difficult to obtain indole of high purity. On the other hand, if higher than 65° C. the effect of sweat-washing becomes too high, lowering the amount of indole of the ultimate product and as a result lowering the yield of high purity indole. The above-mentioned sweat-washing is a phenomenon which takes places when the pressure is lowered after formation of the lumpy solid, and in which impurity-containing surface portions of the lumpy solid are caused to dissolve off upon pressure reduction, and the purity of the lumpy solid is improved further by removal of the dissolved impurity-containing liquid.

When the mixture is fed in the form of slurry, the crystallization of indole in the crystallizing stage is further accelerated and a higher yield can be obtained. Accordingly, it is desirable that, prior to feeding to the high pressure container, the mixture be cooled into a slurry form containing crystalline indole. However, when the amount of crystalline indole is larger than 30 wt %, the mixture might clog the feed pipe which leads to the high pressure vessel. Therefore, it is desirable to hold the amount of crystalline indole less than 30 wt %.

In the stage of solid-liquid separation under pressure, the sweat-washing action takes place each time when the pressure is reduced in the continuous or stepwise pressure reductions. As a result, the purity of the ultimately obtained indole is further improved. Accordingly, it is desirable to reduce the pressure continuously or stepwise as stated hereinbefore.

In this connection, it is preferred that each pressure reduction in the stepwise pressure reductions be of an extremely little extent for the purpose of enhancing the degree of improvement in purity, and therefore the continuous pressure reduction which is the ultimate form of the fine pressure reductions is most preferable.

EXAMPLES

The invention is illustrated more particularly by way of examples based on operations of pressurized crystallization equipments with an inner volume of 20 cc.

EXAMPLE 1

Shown in FIG. 1 are the major components of the above-mentioned equipment. As seen in FIG. 1, the equipment includes a pressure vessel 5 with a piston 3 which is moved vertically up and down in the pressure vessel 5 by a hydraulic unit 1 and which defines a crystallization chamber 6 in the pressure vessel 5. Connected to the crystallization chamber 6 are a raw material liquid feed pipe 8 with a valve 9 and a liquid discharge duct 10 with a valve 11. The piston 3 is provided with a filter 4 to discharge the liquid phase therethrough. The pressure vessel 5 is put in a constant temperature oven 13 which adjusts the crystallization chamber 6 to a predetermined temperature by cooling or heating. In FIG. 1, indicated at 14 is a heater for the constant temperature oven 13, at 15 is a stirrer for the constant temperature oven 13, at 2 is a pressure gauge for measurement of the piston pressure, at 12 is a pressure gauge for measurement of the internal pressure of the crystallization chamber 6, and at 7 is a thermocouple for measuring the temperature.

Separation and refinement of indole was carried out by the use of the above-described equipment. Firstly, the pressure vessel 5 was heated in the constant temperature oven 13 to maintain its interior at the temperature of 50° C. Then, while the valve 11 was held closed, the valve 9 was opened to feed the crystallization chamber 6 with a mixture (raw material) consisting of 69.3 wt % of indole and the balance of quinoline, isoquinoline, monomethylnaphthalene and biphenyl, through the crude liquid feed pipe 8.

As soon as the crystallization chamber 6 was filled with the raw material, the valve 9 was closed, commencing pressurization by the piston 3. The applied pressure was raised to a crystallization level of 2000 atms. Upon raising the pressure, a predetermined solid-liquid ratio (saturation) was reached immediately to complete the crystallization. At this time, the temperature in the crystallization chamber 6 was increased by the latent heat of freezing, which was generated as a result of crystallization. Although the solid-liquid separation would be initiated at this time point in an industrial operation (adiabatic operation), an isothermal operation was carried out in this instance.

More specifically, after waiting until the temperature in the crystallization chamber 6 dropped to 50° C., the valve 11 was opened and the solid-liquid separation was effected at a separation pressure of 2000 atms. Namely, while maintaining the pressure which was applied to the piston 3 by the hydraulic unit 1, the piston 3 was lowered continuously to discharge the liquid phase from the crystallization chamber 6 past the filter 4 and the liquid discharge duct 10. The piston 3 was lowered further to press the crystal grains in the crystallization chamber 6, thereby discharging the residual liquid lingering between individual crystal grains by the so-called "squeezing action".

In the next place, the lowering of the piston 3 was stopped and, after reducing the pressure to normal level, the piston 3 was moved upward. The solid product which remained in packed state in the crystallization chamber 6 was taken out and recovered. The recovered solid product had a weight corresponding to 28% of the mixture which had been fed to the crystallization chamber 6. The indole concentration in the solid was 99.2%, succeeding in obtaining indole of extremely high purity.

EXAMPLE 2

Separation and refinement of indole was carried out in the same manner as in Example 1 except for certain conditions. Namely, Example 1 was repeated with respect to the crystallization equipment, composition of the feed material, and the conditions in the stages of material injection (feed) and separation, discharge and squeezing-out of the liquid phase after crystallization. After squeezing out the liquid phase under the same condition as in Example 1, the downward movement of the piston 3 was stopped and, the piston pressure was lowered and maintained at 500 atms. for a sweat-washing treatment.

After the sweat-washing treatment, the piston 3 was moved up, and the solid product in the crystallization chamber 6 was recovered. The recovered solid product had a weight corresponding to 25.5% of the mixture which had been fed to the crystallization chamber 6. The indole concentration in the recovered solid was 99.7%, which was higher than in Example 1, thus succeeding in obtaining indole of extremely high purity.

COMPARATIVE EXAMPLE 1

Separation and refinement of indole was carried out with use of the same equipments as in Example 1. More specifically, a mixture consisting of 40 wt % of indole and the balance of quinoline, isoquinoline, monomethylnaphthalene and biphenyl was fed to the high pressure vessel which was maintained at the temperature of −10° C. The pressure in the vessel was raised to a crystallizing level of 1500 atms. for crystallization of indole, and then that pressure (1500 atms) was maintained as a separation pressure in the succeeding solid-liquid separation treatment thereby discharging the liquid phase from the container. Thereafter, the pressure was lowered to normal level, and the piston 3 was moved upward for recovering the solid product. However, instead of the lumpy solid, the crystal grains were in the form of sherbet-like solid, and thus it was impossible to recover indole of solid form. This was considered to be attributable to the small proportion of indole in the feed material, which was less than 50 wt %.

Thus, the indole separating and refining process according to the present invention makes it possible to obtain indole of high purity by separation and refinement of a simple process. Besides, it becomes possible to shorten the operational time for the separation and refinement, in addition to the improvement in operational safety.

What is claimed is:

1. A process for separating indole in refined form, by feeding a mixture containing more than 50 wt % of indole to a high pressure vessel, pressurizing said mixture in said high pressure vessel to crystallize indole, conducting solid-liquid separation continuously in pressurized state, and removing solid indole of a purity of more than about 99% from said high pressure vessel, characterized in that:

a pressure of 700–2500 atms is applied for crystallization of indole in said high pressure vessel; and the operating temperature of said solid-liquid separation is in the range of 50°–65° C.

2. A process as defined in claim 1, further comprising cooling said mixture into a slurry form containing less than 30 wt % of crystalline indole prior to feeding same to said high pressure vessel.

3. A process as defined in claim 2, wherein said solid-liquid separation is conducted with continuous or stepwise pressure reductions.

* * * * *

UNITED STATES PATENT AND TRADEMARK OFFICE
CERTIFICATE OF CORRECTION

PATENT NO. : 4,966,978

DATED : OCTOBER 30, 1990

INVENTOR(S) : YOSHIKI SATO ET AL

It is certified that error appears in the above-identified patent and that said Letters Patent is hereby corrected as shown below:

On the title page, as Item 73, "Assignee", there should be added -- and Agency of Industrial Science and Technology, Tokyo, Japan--.

Signed and Sealed this

Fifth Day of May, 1992

*Attest:*

DOUGLAS B. COMER

*Attesting Officer*

*Acting Commissioner of Patents and Trademarks*